United States Patent [19]
Dyson-Cantwell et al.

[11] Patent Number: 5,478,310
[45] Date of Patent: Dec. 26, 1995

[54] DISPOSABLE HYPERBARIC OXYGEN CHAMBER

[76] Inventors: Evelyna Dyson-Cantwell; John W. Cantwell; Madalene C. Y. Heng, all of 101 Hickory Hill Rd., Chadds Ford, Pa. 19317

[21] Appl. No.: 216,407
[22] Filed: Mar. 23, 1994
[51] Int. Cl.$^6$ .......................... A61M 37/00; A61M 35/00
[52] U.S. Cl. ................................ 604/23; 604/293; 2/79; 2/227
[58] Field of Search ........................ 604/290, 292, 604/293, 23–26, 317, 333, 337; 601/11, 43, 44, 48, 166; 2/59, 60, 79, 227; 600/21

[56] References Cited

U.S. PATENT DOCUMENTS

| | | | |
|---|---|---|---|
| 2,168,611 | 8/1939 | Thompson | 604/293 X |
| 3,744,491 | 7/1973 | Fischer | 604/293 X |
| 4,003,371 | 1/1977 | Fischer | 604/293 X |
| 4,224,941 | 9/1980 | Stivala | 604/293 X |
| 4,236,513 | 12/1980 | Lo Piano | 604/293 |
| 4,296,743 | 10/1981 | Lasley | 601/11 X |
| 4,331,148 | 5/1982 | Steer et al. | 604/333 |
| 4,432,354 | 2/1984 | Lasley | 601/43 |
| 4,772,259 | 9/1988 | Frech et al. | 604/293 X |
| 4,911,699 | 3/1990 | Fenton | 604/333 |
| 5,029,579 | 7/1991 | Trammell | 601/43 X |
| 5,256,159 | 10/1993 | Newman | 604/317 |
| 5,411,496 | 5/1995 | Homa | 604/333 |

FOREIGN PATENT DOCUMENTS 114443 12/1941 Australia ............................... 604/290

OTHER PUBLICATIONS

Madalene C. Y. Heng, A Simplified Hyperbaric Oxygen Technique for Leg Ulcers, *Arch Dermatol*, vol. 120, May 1984, pp. 640–645.

*Primary Examiner*—Mary Beth O. Jones
*Attorney, Agent, or Firm*—Norman E Lehrer

[57] ABSTRACT

A disposable hyperbaric oxygen chamber includes a polyethylene bag which is substantially the length of a patient's leg and which is placed around the entire leg and thigh with the excess bag at the top thereof being folded over the thigh in order to fit snugly thereon without compression. A length of nonstretchable tape seals the top of the bag around the upper thigh just below the inguinal ligament. Another circumferential layer of tape is applied to the top of the bag to attach the same to the patient's pants to prevent displacement of the bag as the patient moves around. In an alternative embodiment, the bag may be preformed into the leg of a pair of disposable shorts to be worn by the patient. Oxygen is fed to the bag through the use of a hose connector secured to the bag. After the bag has been inflated with oxygen, the tubing may be clamped off and removed so that the patient can move about freely.

13 Claims, 3 Drawing Sheets

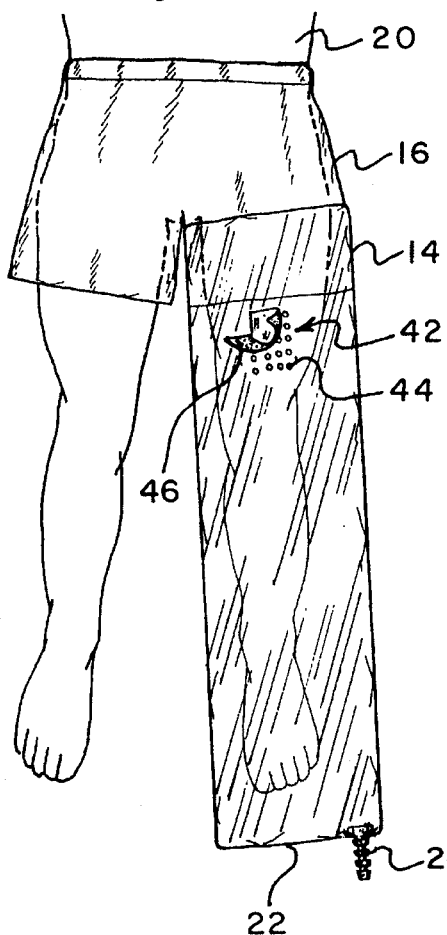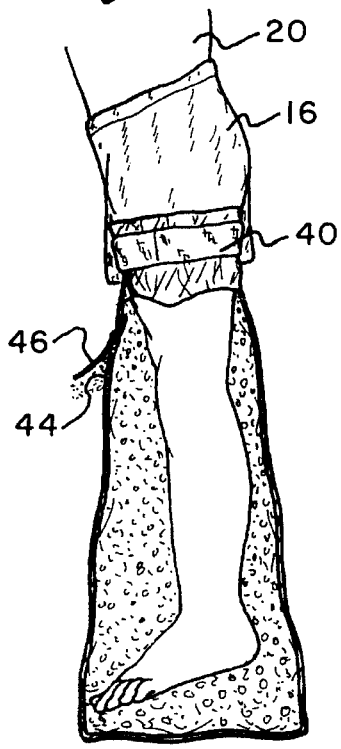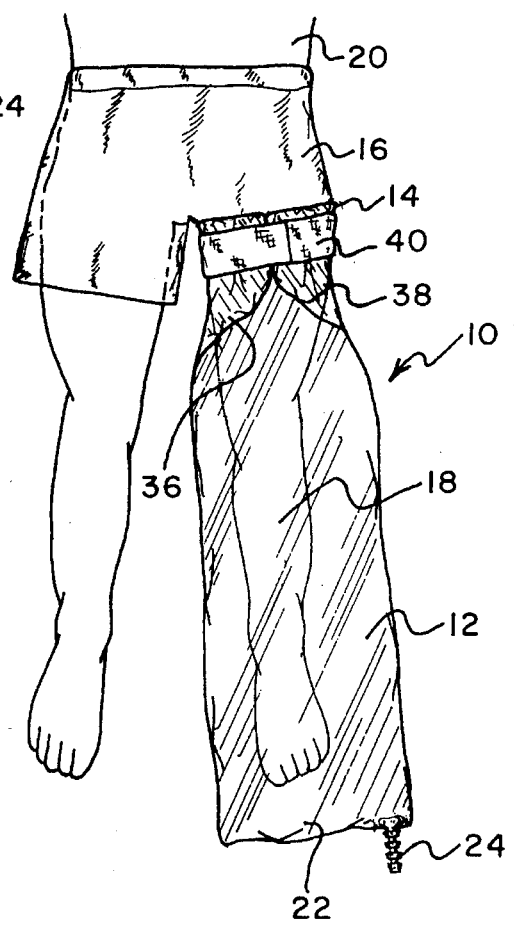

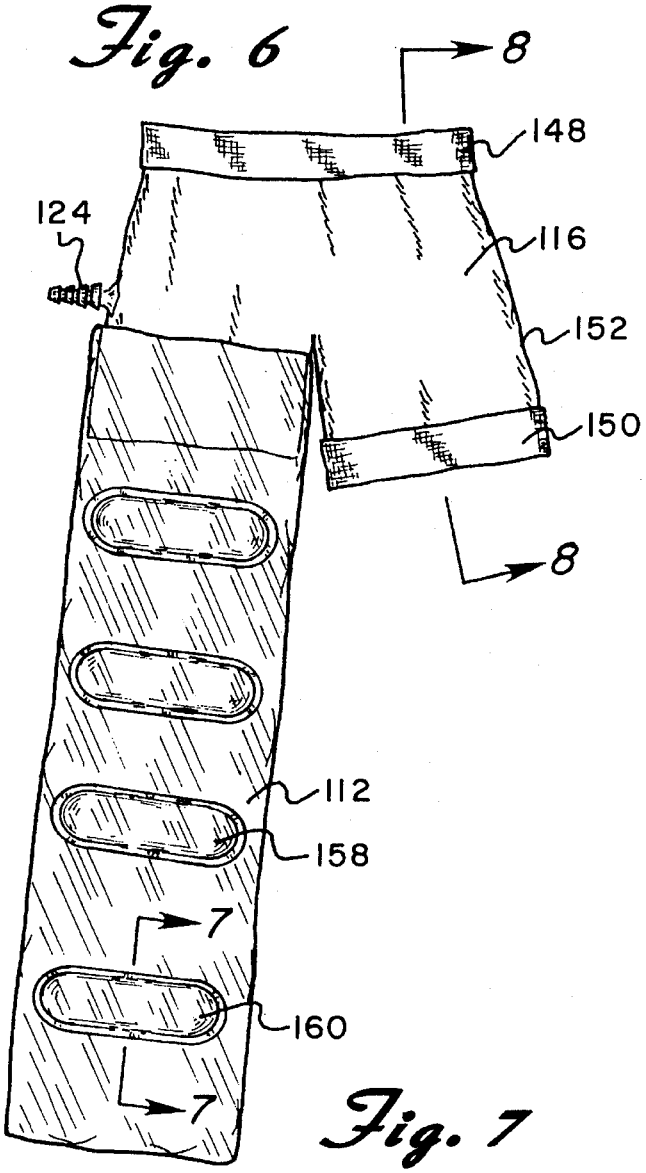
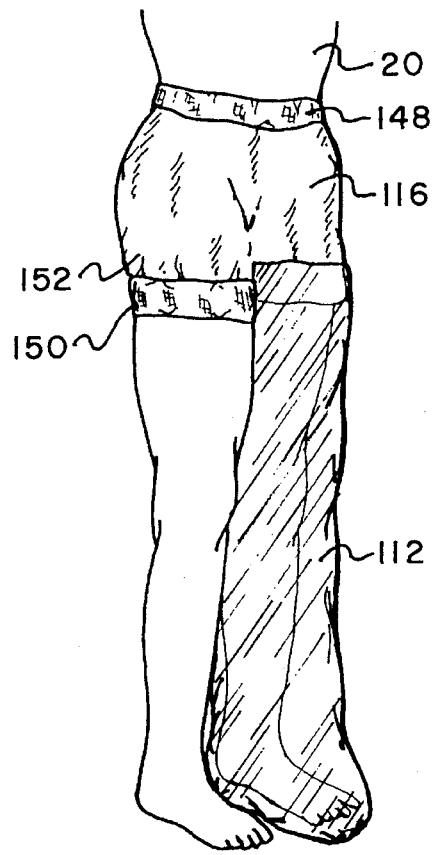
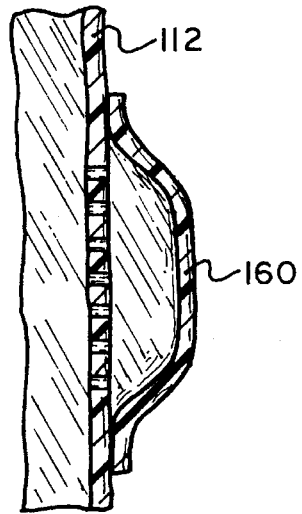
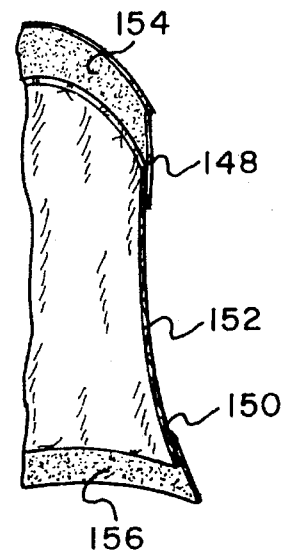

5,478,310

DISPOSABLE HYPERBARIC OXYGEN CHAMBER

BACKGROUND OF THE INVENTION

The present invention is directed toward hyperbaric apparatus for applying oxygen to leg wounds and, more particularly, to a disposable, inflatable hyperbaric chamber and to a method of applying and utilizing the same.

As is well known in the art, hyperbaric chambers are devices which create sealed and pressurized environments for the treatment of lesions and wounds on a patient's body. It has been well established that hyperbaric oxygen is an effective treatment for wounds as the same induces the growth of new blood vessels or neovascularization necessary for stimulating the growth of new tissue in order to close defects in wounds.

Devices have been proposed in the past for treating leg ulcers or other leg wounds utilizing hyperbaric oxygen. These prior devices are comprised essentially of a rigid chamber having an opening at one end through which the leg can be inserted. Such prior hyperbaric chambers are described, for example, in U.S. Pat. No. 4,003,371 to Fischer and U.S. Pat. Nos. 4,296,743 and 4,432,353 to Lasley.

The prior art hyperbaric oxygen chambers such as those proposed by Fischer and Lasley are relatively expensive and are difficult to sterilize, thereby creating cross-infection between patients using the same chambers for therapy. Furthermore, these prior art chambers were relatively large, rigid and immovable. Accordingly, during treatment, the patient was required to lie in a prone position at all times.

In an article published by Heng et al. in *Arch Dermatol* in 1984, a technique for administering hyperbaric oxygen is disclosed which utilizes a disposable polyethylene bag. This technique has the advantage of being substantially simpler than more complex hyperbaric oxygen chambers and is less likely to cause cross-infection. The technique previously proposed by Heng et al., however, is still believed to be deficient in the manner in which the bag is closed and secured to the patient and in the inability to allow the patient to be ambulatory while receiving treatment.

A similar problem exists with the apparatus shown in U.S. Pat. No. 5,029,579 to Trammell. Trammell discloses an arrangement which utilizes a flexible disposable bag but which must be continuously connected to a pulsating oxygen source. As a result, the patient can not be ambulatory. Furthermore, in both the Heng et al. and Trammell arrangements, there is no easy and convenient way of securing the flexible bag to the patient's leg.

SUMMARY OF THE INVENTION

The present invention overcomes the deficiencies of the prior art described above and provides a hyperbaric oxygen chamber for treating leg wounds which is disposable and which, if desired, allows the patient to be ambulatory while treatment is being applied. The chamber is comprised essentially of a disposable polyethylene bag which is substantially the length of the patient's leg and which is placed around the entire leg and thigh.

The excess bag at the top is gathered into two pleats on the medial and lateral side of the thigh and these pleats are folded over in front of the thigh to cause the bag to fit snugly but without compression over the thigh. Tape seals the top of the bag around the upper thigh just below the inguinal ligament. The tape is placed circumferentially around the bag and is positioned to fall within the inguinal triangle which is the space bounded by the inguinal ligament superiorly, rectus femoris laterally and obturator muscles medially. Another circumferential layer of tape is applied to attach the top end of the bag to the patient's pants to prevent displacement of the bag as the patient moves around.

Alternatively, the bag may be preformed onto the leg of a pair of disposable short pants to be worn by the patient. The bag can be secured to the leg with a circumferential layer of tape or the shorts can be made of an air impermeable material and include an adhesive waistband and adhesive band at the bottom of the other leg. Oxygen is fed to the bag through the use of a hose or tubing connector welded or otherwise secured to the bag or to the shorts. After the bag has been inflated with oxygen to the proper pressure level, the tubing can be clamped off so that the patient can move about freely.

BRIEF DESCRIPTION OF THE DRAWINGS

For the purpose of illustrating the invention, there are shown in the accompanying drawings forms of the invention which are presently preferred; it being understood that the invention is not intended to be limited to the precise arrangements and instrumentalities shown.

FIG. 3 is a view similar to FIG. 2 but showing the combined shorts and disposable hyperbaric oxygen chamber applied to a patient's leg;

FIG. 4 is a view similar to FIG. 3 but showing the manner in which the top of the bag is gathered and secured to the patient's thigh;

FIG. 5 is a side view similar to FIG. 1 showing the chamber filled with oxygen;

FIG. 6 is a view similar to FIG. 3 but showing rear view a modified form of the invention;

FIG. 7 is a cross-sectional view taken along the line 7—7 of FIG. 6;

FIG. 8 is a cross-sectional view taken along the line 7—7 of FIG. 6, and

FIG. 9 is a perspective view of the modified form of the invention in use.

DETAILED DESCRIPTION OF THE PREFERRED EMBODIMENT

Figure 1:
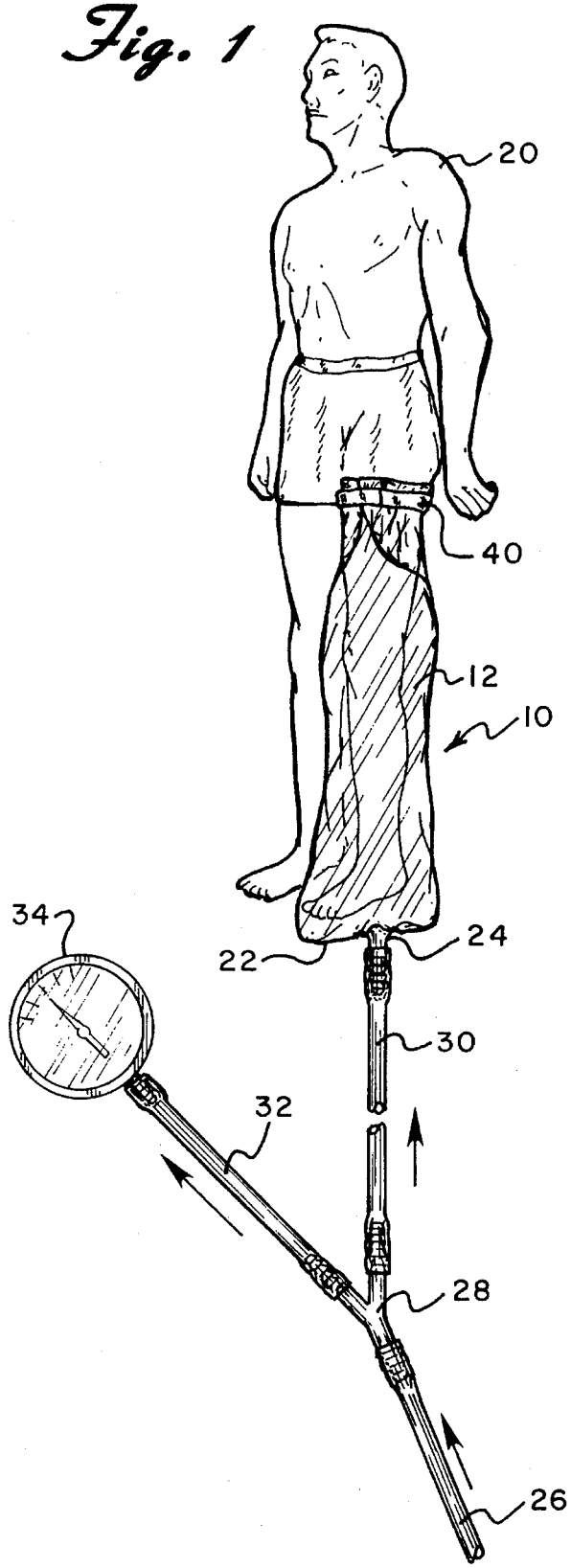
FIG. 1 is a perspective view of a disposable hyperbaric oxygen chamber constructed in accordance with the principles of the present invention and being shown applied to a patient.
Figure 2:
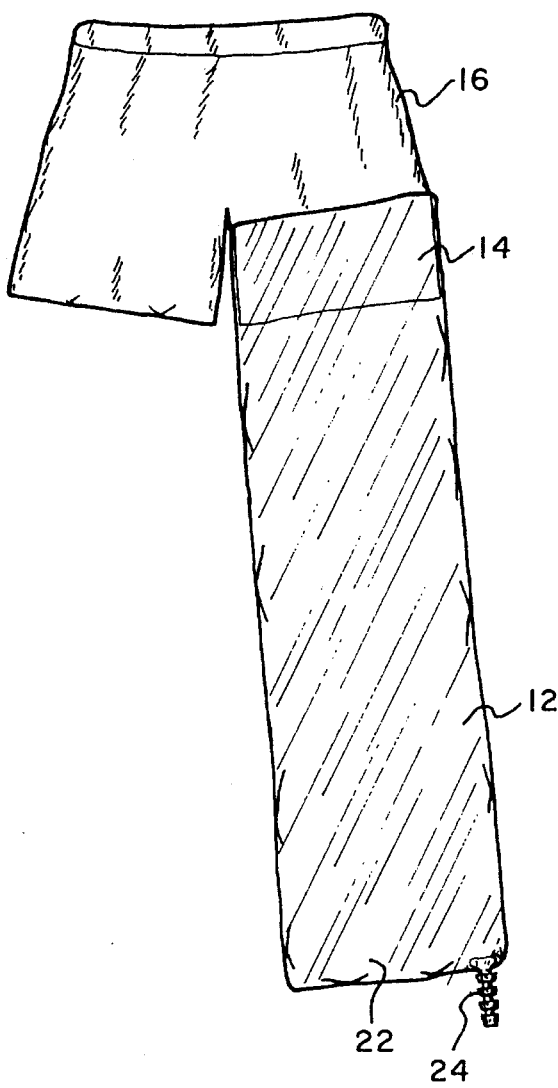
FIG. 2 is a front view of one form of a hyperbaric oxygen chamber in accordance with the invention being preliminarily attached to a pair of disposable shorts.

Referring now to the drawings in detail wherein like reference numerals have been used throughout the various figures to designate like elements, there is shown in the figures a disposable hyperbaric oxygen chamber constructed in accordance with the principles of the present invention and designated generally as 10. In one form of the invention shown in FIGS. 1–5, the disposable hyperbaric oxygen chamber 10 is comprised of an elongated and disposable polyethylene bag 12 having its upper open end 14 heat welded or otherwise secured to the open pant leg of a pair of disposable shorts 16. It should be understood, however, that this is by way of example only. An aspect of the invention can also be practiced utilizing only the polyethylene bag 12 without the disposable shorts 16.

As shown in FIGS. 1 and 3–5, the bag 12 is large enough to totally enclose the entire leg 18 of a patient 20. Bag 12 is also preferably made to be transparent so that a doctor can observe the healing process of the wound being treated. Attached to the lower end 22 of the bag 12 is a hose or tubing connector 24 which allows a source of oxygen under pressure (not shown) to communicate with the interior of the bag 12 through appropriate tubing assembly 26 as shown in FIG. 1. The tubing assembly 26 preferably includes a Y-connector 28 which allows one branch 30 of the tubing to be connected to the bag 12 while the other branch 32 of the tubing can be connected to a pressure gauge 34 or the like. In lieu of the pressure gauge 34, the connector 24 or some other portion of the bag 12 may be provided with a built in pressure gauge or indicator. Devices are known which, for example, emit an audible sound or automatically close when a predetermined and preset pressure level is reached.

For the reasons which will become clearer hereinafter, the connector 24 may also include a one-way valve therein. That is, it may include a valve which allows oxygen under pressure to enter the bag 12 but which prevents oxygen from escaping therethrough. Such valves are, per se, well known in the art as shown in U.S. Pat. No. 2,168,611 to Thompson.

The disposable hyperbaric oxygen chamber 10 described above is used in the following manner. First, the leg bandages are removed from the patient so as to expose the ulcer or other wound being treated. The polyethylene bag 12 is then placed around the entire leg and thigh. If the embodiment of the invention utilizing the combined bag and shorts 16 is utilized, this is accomplished by having the patient put the shorts on and pull them up to the proper position.

Whether or not the shorts 16 are utilized, the upper end of the bag is pulled up against the buttocks as high as possible. The top open end of the bag (again with or without the shorts attached) is stretched laterally and the excess width is gathered into two pleats 36 and 38, one on the medial side and one on the lateral side of the thigh. The pleats 36 and 38 are then folded over in front of the thigh to cause the top of the bag 12 (whether or not already attached to the shorts 16) to fit snugly, without compression, over the thigh and tape is utilized to keep the pleats in place. The top end of the bag 12 is then sealed around the upper thigh just below the inguinal ligament. This is accomplished utilizing a length of nonstretchable tape 40 that is placed circumferentially along the top of the open end 14 of the bag 12 and over the pleats.

The layer of tape 40 must be arranged so that it falls within the inguinal triangle which is the space bounded by the inguinal ligament superiorly, rectus femoris laterally and the obturator muscles medially. The tape should be sufficiently tight so as to provide a substantial seal in order to prevent excessive leakage of oxygen from the bag 12 during therapy. However, because of the specific placement of the tape, blood flow to and from the leg is not restricted.

With respect to the embodiment of the invention which does not utilize the bag 12 permanently secured to the disposable shorts 16, a second circumferential layer of tape is preferably applied in order to attach the top end 14 of the bag 12 to the patient's shorts or other clothing. Attaching the top of the bag to the shorts 16 or by the use of an additional layer of tape to the patient's normal clothing prevents displacement of the disposable hyperbaric oxygen chamber when the patient moves around during treatment.

The bag 12 is then filled with oxygen through tubing assembly 26 utilizing either a conventional oxygen delivery system or a specially designed single use source. When the bag is substantially full, the pressure of the oxygen is regulated to be between approximately 25–30 mmHg for arterial ulcers, burns and pyoderma gangrenosum and preferably between 18–20 mmHg for venous ulcers. The bag is then depressed slightly to check for leaks so as to be certain that the interior pressure is substantially maintained. If no leaks are sensed, the tube 30 can be removed from the connector 24 if the connector includes a one-way valve therein. If such a valve is not utilized, then the tubing 30 can be clamped off and removed from the Y-connector 28. In any case, the patient is then free to move about.

It has been found that the best results are obtained if the hyperbaric oxygen therapy is applied for four to six hours per day. This is done on four consecutive days during each week with a three-day rest period and is continued for three to six weeks.

The bag 12 is preferably made of polyethylene or a similar material which is impervious to fluids (particularly oxygen) so as to maintain the oxygen pressure within the bag at the desired level. There may be times, however, when it may be desired to lower the pressure within the bag or reduce the amount of oxygen. To this end, the disposable hyperbaric oxygen chamber 10 may include a bleed valve 42.

In its simplest form, bleed valve 42 is comprised of a plurality of small holes 44 formed in a portion of the bag 12. The holes 44 are normally covered by a flap of material 46 having a releasable adhesive backing thereon. The flap 46 normally covers all of the holes 44. However, if it is ever desired to reduce the pressure in the disposable hyperbaric oxygen chamber, the flap 46 can be pulled back to expose some or all of the holes 44 to allow some of the oxygen to escape. When the proper pressure is reached, the flap 46 is resealed.

In order to eliminate or substantially reduce odors that may form within the bag during the treatment period, the bag may be made from or lined with a deodorant material. Finely ground carbon powder, for example, coated on the inside of the bag will absorb foul odors. Other materials and other means of eliminating odors may also be used.

Another embodiment of the disposable hyperbaric oxygen chamber is shown in FIGS. 6, 7 and 8. The embodiment shown therein is similar to the previous embodiment except that the shorts 116, to which the bag 112 is attached, are made of an air impermeable material. The waistband 148 of the shorts and bottom 150 of the free leg 152 have adhesive on the inner surface thereof as shown at 154 and 156, respectively. In the manner well known in the art, the adhesive bands 154 and 156 are normally covered with a release strip which can be removed to expose the adhesive. Since the shorts 116 are also made of an air or oxygen impermeable material, the hose or tubing connector 124 can be attached directly thereto.

Located on the back of the bag 112 are a plurality of inflatable pillows such as show at 158 and 160. These pillows are preferably formed integrally with the bag although it is possible to attach them after the bag is formed. In any case, the pillows 158 and 160 are filled with air or oxygen. There may be small passages formed between the interiors of the pillows and the bag 112 so that the pillows are inflated as the bag is filled with oxygen. Alternatively, the pillows may be prefilled with air or can be provided with separate fill valves.

The embodiment of the invention shown in FIGS. 5–8 is used in a manner similar to the first embodiment described above. It is not necessary, however, to seal the top of the bag 112 around the patient's thigh. Rather, after the patient puts the shorts 116 on, the release material is removed and the adhesive 154 and the waistband 148 is then firmly sealed around the patient's waist. Similarly, the adhesive 156 is exposed and the lower end 150 of the leg 152 is sealed around the patient's leg that is not being treated. Oxygen is then introduced through the connector 124 above.

It should be readily apparent that the embodiment of the invention just described can also be used to treat sores and the like on a patient's buttocks or lower abdomen since oxygen will also fill the shorts 116. Furthermore, it is not beyond the scope of the invention to provide the shorts 116 with two bags, one for each leg. With such an arrangement, the shorts would be provided with adhesive only at the waistband. In either case, the shorts and the bag or bags can be formed separately and later joined together or they can be formed in a single piece.

The present invention may be embodied in other specific forms without departing from the spirit or essential attributes thereof and accordingly reference should be made to the appended claims rather than to the foregoing specification as indicating the scope of the invention.

We claim:

1. A method of healing a leg wound on a human patient utilizing hyperbaric oxygen comprising:

providing a flexible gas impermeable plastic bag of a size sufficiently large enough to totally encompass a patient's leg;

inserting the patient's leg into said bag so that said bag is around the patient's entire leg and thigh;

gathering the top of said bag into pleats and folding them over the remaining parts of the upper part of said bag so as to make the top of said bag fit snugly around the patient's thigh;

sealing the top of said bag around the patient's thigh by encircling the top of said bag with nonstretchable tape, said tape being arranged so that it falls within the inguinal triangle of the patient's thigh;

inflating said bag with oxygen to a pressure of approximately 18–30 mmHg, and removing the supply of oxygen to said bag while preventing oxygen from flowing out of said bag.

2. The invention as claimed in claim 1 wherein said bag is allowed to remain in place so as to provide oxygen to the leg for approximately four to six hours.

3. The invention as claimed in claim 2 wherein the application of oxygen for approximately four to six hours is repeated on each of four consecutive days.

4. The invention as claimed in claim 1 wherein said bag is substantially transparent.

5. The invention as claimed in claim 1 wherein said bag is comprised of polyethylene.

6. The invention as claimed in claim 1 wherein said bag includes means for eliminating odors therein.

7. A disposable hyperbaric oxygen chamber comprising a flexible substantially transparent plastic bag, said bag being of sufficient size so as to encompass a patient's entire leg and thigh and a tubing connector secured to a portion of said bag, said connector being adapted to be connected to a length of plastic tubing so as to permit oxygen from within said tubing to pass into the interior of said bag and wherein said bag includes means for eliminating odors therein, said chamber further including a pair of disposable shorts and wherein said bag includes an open upper end thereof, said open end of said bag being permanently secured to one leg of said shorts.

8. A disposable hyperbaric oxygen chamber comprising:

a pair of disposable shorts comprised of a substantially fluid impervious material, said shorts including a waist band for encircling and engaging a patient's waist and first and second leg openings;

a flexible substantially transparent plastic bag, said bag being of sufficient size so as to substantially encompass a patient's entire leg, said bag having a normally open upper end which is secured to said first leg opening so that the interior of said bag is in fluid communications with the interior of said shorts, and a tubing connector secured to a portion of one of said bag and said shorts, said connector being adapted to be connected to a length of plastic tubing so as to permit oxygen from within said tubing to pass into the interior of said bag and said shorts.

9. The invention as claimed in claim 8 wherein said connector includes a one-way valve therein adapted to prevent oxygen within said bag from passing out of said connector to the exterior thereof.

10. The invention as claimed in claim 8 wherein said bag includes means for eliminating odors therein.

11. A disposable hyperbaric oxygen chamber comprising a flexible substantially transparent plastic bag, said bag being of sufficient size so as to encompass a patient's entire leg and thigh and a tubing connector secured to a portion of said bag, said connector being adapted to be connected to a length of plastic tubing so as to permit oxygen from within said tubing to pass into the interior of said bag, said chamber further including a pair of disposable shorts and wherein said bag includes an open upper end thereof, said open end of said bag being permanently secured to one leg of said shorts.

12. The invention as claimed in claim 11 wherein said bag includes means for eliminating odors therein.

13. The invention as claimed in claim 11 wherein said connector includes a one-way valve therein adapted to prevent oxygen within said bag from passing out of said connector to the exterior thereof.

* * * * *